United States Patent [19]

Teraji et al.

[11] Patent Number: 4,957,537
[45] Date of Patent: Sep. 18, 1990

[54] METHOD FOR REGULATING PLANT GROWTH

[75] Inventors: Tsutomu Teraji, Osaka; Atsushi Yamamura, Ibaraki; Yasuo Kamuro, Tsukuba; Koichi Hirai, Hanyu; Seiichi Fujii, Oomiya, all of Japan

[73] Assignees: Fujisawa Pharmaceutical Company, Ltd, Osaka; Nissan Chemical Industries, Ltd., Tokyo, both of Japan

[21] Appl. No.: 171,799

[22] Filed: Mar. 22, 1988

[30] Foreign Application Priority Data

Mar. 24, 1987 [JP] Japan .................... 62-69370

[51] Int. Cl.$^5$ ............................................. A01N 37/32
[52] U.S. Cl. ........................................ 71/95; 548/544; 548/545; 548/548
[58] Field of Search .................................... 71/95

[56] References Cited

U.S. PATENT DOCUMENTS

| | | | |
|---|---|---|---|
| 2,865,730 | 12/1958 | Gates et al. | 71/95 |
| 4,191,555 | 3/1980 | Kliegman | 71/95 |
| 4,643,762 | 2/1987 | Ward | 71/95 |

FOREIGN PATENT DOCUMENTS

| | | |
|---|---|---|
| 44-8499 | 4/1969 | Japan . |
| 45-4063 | 2/1970 | Japan . |
| 45-11893 | 4/1970 | Japan . |
| 45-18654 | 6/1970 | Japan . |
| 45-23559 | 8/1970 | Japan . |

OTHER PUBLICATIONS

Bulletin-Plant Growth Regulator, vol. 13, No. 3, Jul.-Sep. 1985, pp. 7-13.
George C. Martin, "Mechanical Fruit Harvest: Resources, Energy Conduction, and Use of Loosening Agents".

*Primary Examiner*—David B. Springer
*Attorney, Agent, or Firm*—Oblon, Spivak, McClelland, Maier & Neustadt

[57] ABSTRACT

The present invention discloses a new plant growth regulating composition which comprises, as an active ingredient, a selected succinamide compounds, maleimide compounds, succinic anhydride compounds, maleic anhydride compounds of general formula:

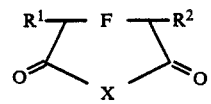

if preferably, along with ethephon. In this invention, the plant growth regulating composition has the effect of plant growth controlling activity (herbicidal activity) and an abscission layer forming activity for a fruit harvest aid, and the said plant growth regulating composition does not cause hazards such as defoliation and injuries to the fruit surface, nor does it affect immature fruit, but acts specifically on matured fruit and promptes formation of abscission layer that aids in the separation of matured fruit.

12 Claims, No Drawings

METHOD FOR REGULATING PLANT GROWTH

BRIEF SUMMARY OF THE INVENTION

As a plant growth regulating agent being adapted for promoting formation of the abscission layer for facilitating abscission of matured fruit, ethephon or the like has heretofore been employed but such known agents produce either phytotoxic effects(defoliation and hazards to the fruit surface) or promiscuous effects on immature fruit. Therefore, there has been a demand for new plant growth regulators either completely or virtually free of such disadvantages.

A main object of the present invention is to provide a new plant growth regulating composition which has a plant growth controlling activity (herbicidal activity) and an abscission layer forming activity for a fruit harvest aid, which does not cause hazards such as defoliation and injuries to the fruit surface, nor does it affect immature fruit, but acts specifically on matured fruit and promotes formation of an abscission layer that aids in the separation of matured fruit. Another object of the invention is to provide a new method for regulating plant growth including an abscission layer formation for a fruit harvest aid. Further objects and advantages of the present invention will become more apparent from the following descriptions.

DETAILED DESCRIPTION OF THE INVENTION

The inventive research which the present inventors conducted to overcome the above-mentioned disadvantages led to the finding that the selected succinamide compounds, maleimide compounds, succinic anhydride compounds, maleic anhydride compounds of the following general formula (I) does not cause hazards such as defoliation and injuries to the fruit surface, nor does it affect immature fruit, but acts specifically on matured fruit and promotes formation of an abscission layer that aids in the separation of matured fruit. It was also found that when used in combination with ethephon, said compound of the following general formula (I) exhibits synergism and that the compound of the following general formula (I) has plant growth controlling activity (herbicidal activity) as well. The present invention has been accomplished on the basis of the above findings.

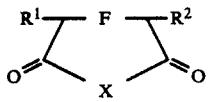

wherein $R^1$ is a hydrogen atom, a lower alkyl group or a phenyl group which may optionally be substituted by one or more substituents selected from the class consisting of nitro, halogen, lower alkyl and lower alkoxy; $R^2$ is a hydrogen atom, a halogen atom, a lower alkoxy group, a lower alkylthio group which may optionally be substituted by lower alkoxycarbonyl, a phenylthio group which may optionally be substituted by halogen or lower alkyl, a phenylamino group, a phenylsulfonyl group or a heterocyclethio group which may optionally be substituted by lower alkyl; X is an oxygen atom or a group of the formula N—Z (wherein Z is a hydrogen atom; a lower alkyl group which may optionally be substituted by hydroxy or lower alkanoyloxy; a phenyl group which may optionally be substituted by one or more substituents selected from the class consisting of carboxy, hydroxy, halogen, nitro, lower alkyl and lower alkoxy; a phenoxy group; a cyclohexyl group or a group of the formula

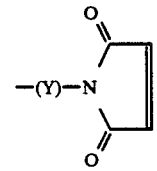

where Y is a group of the formula

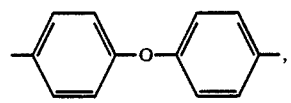

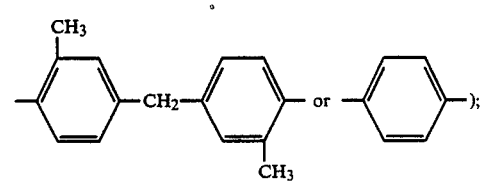

F means a single bond or a double bond.

The compound of general formula (1) to be contained as an active ingredient in the plant growth regulating composition of the invention includes both new and known compounds and the new compounds can be produced by processes analogous to the production processes described in the literature cited hereinafter or by the processes described in the production examples which appear hereinafter.

The definitions used in this specification for describing the compound of general formula (I) are as follows.

The term "lower" refers, unless otherwise indicated, to a group consisting of 1 to 6 carbon atms.

The term "lower alkyl" means a straight-chain or branched saturated lower aliphatic hydrocarbon residue and includes such preferred species as methyl, ethyl, propyl, isopropyl, butyl, isobutyl, tert-butyl, pentyl and hexyl.

The term "lower alkoxy" means a group derived as a straight-chain or branched saturated lower aliphatic hydrocarbon residue is united with an oxygen atom and includes such preferred species as methoxy, ethoxy, propoxy, isopropoxy, butoxy, isobutoxy, tert-butoxy, pentyloxy and hexyloxy.

The term "halogen" includes fluorine, chlorine, bromine and iodine.

The term "lower alkylthio" means a group derived as a straight-chain or branched saturated lower aliphatic hydrocarbon group is united with a sulfur atom and includes such preferred species as methylthio, ethylthio, propylthio, isopropylthio and butylthio.

Preferred examples of "lower alkoxycarbonyl" include methoxycarbonyl, ethoxycarbonyl, propoxycarbonyl, isopropoxycarbonyl, isobutoxycarbonyl and tert-butoxycarbonyl.

Preferred examples of "heterocyclethio" include 5- or 6-membered unsaturated heterocyclethio groups each containing at least one nitrogen atom as the heteroatom (for example, pyrazolinylthio, pyridylthio, pyrimidylthio, etc) and 5- or 6-membered unsaturated heterocyclethio groups each containing at least one nitrogen atom and one sulfur atom as hetero-atoms (for example, thiazolylthio, thiadiazolylthio, etc.).

Preferred examples of "lower alkanoyloxy" include acetoxy, propionyloxy, butyryloxy, and isobutyryloxy.

The following is a list of representative species of the compound (I) which is used as the active ingredient in the plant growth regulating composition according to the invention. (The compound numbers correspond to the numbers given in tables in the test examples which appear hereinafter. The abbreviation J.P. Publ. stands for Japanese Patent Publication. The abbreviation S. and D. stands respectively for a single and a double bond.)

| Compound No. | $R^1$ | $R^2$ | X | F | Literature or m.p. (°C.) |
|---|---|---|---|---|---|
| 1 | 4-Cl-C6H4 | Cl | NH | S. | J.P. Publ. 45-23559 |
| 2 | 2-Cl-C6H4 | H | NH | D. | J.P. Publ. 45-23559 |
| 3 | 2-Cl-C6H4 | OCH$_2$CH$_3$ | NH | S. | 175 |
| 4 | 2-Cl-C6H4 | NH-C6H5 | NH | S. | (Production Example 17) |
| 5 | 2-Cl-C6H4 | SCH$_2$COOCH$_2$CH$_3$ | NH | S. | 115–118 |
| 6 | 2-Cl-C6H4 | S(CH$_2$)$_3$CH$_3$ | NH | S. | 70–72 |
| 7 | 2-Cl-C6H4 | -S-thiadiazolyl | NH | S. | 195–200 |
| 8 | 2-Cl-C6H4 | -S-pyrimidinyl | NH | S. | 158–160 |
| 9 | 2-Cl-C6H4 | -S-C6H5 | NH | S. | 77–83 |
| 10 | 2-Cl-C6H4 | -S-C6H4-Cl | NH | S. | 40–50 |
| 11 | 2-Cl-C6H4 | -S-C6H4-CH$_3$ | NH | S. | 44–55 |

-continued

| Compound No. | R¹ | R² | X | F | Literature or m.p. (°C.) |
|---|---|---|---|---|---|
| 12 | 2,4-dichlorophenyl | H | NH | D. | J.P. Publ. 45-23559 |
| 13 | 3-chlorophenyl | -S-phenyl | NH | S. | 104–106 |
| 14 | 4-chlorophenyl | -S-phenyl | NH | S. | J.P. Publ. 44-8499 |
| 15 | phenyl | -S-phenyl | NH | S. | 109–112 |
| 16 | 4-methylphenyl | -S-phenyl | NH | S. | 130–134 |
| 17 | 2-methoxyphenyl | -S-phenyl | NH | S. | 108–110 |
| 18 | 4-methoxyphenyl | -S-phenyl | NH | S. | 108–110 |
| 19 | 2-nitrophenyl | -S-phenyl | NH | S. | (Production Example 11) |
| 20 | 4-nitrophenyl | -S-phenyl | NH | S. | 142–145 |
| 21 | 2-chlorophenyl | -S-C(S)=N-N=C(CH₃)- (1,3,4-thiadiazole) | NH | S. | 189–193 |
| 22 | 2-chlorophenyl | H | N—CH₂CH₂OH | D. | P.P. Publ. 45-18654 |
| 23 | 2-chlorophenyl | H | N—CH₂CH₂OCOCH₃ | D. | J.P. Publ. 45-11893 |
| 24 | 2-chlorophenyl | H | N-piperidinyl (NH) | D. | (Production Example 21) |

-continued

| Compound No. | R¹ | R² | X | F | Literature or m.p. (°C.) |
|---|---|---|---|---|---|
| 25 | 2,5-dichlorophenyl | H | N—CH$_2$CH$_2$OH | D. | J.P. Publ. 45-18654 |
| 26 | 2,5-dichlorophenyl | H | N—CH$_2$CH$_2$OCOCH$_3$ | D. | J.P. Publ. 45-11893 |
| 27 | 2,5-dichlorophenyl | H | N-cyclohexyl | D. | J.P. Publ. 45-4063 |
| 28 | 2-chlorophenyl | H | O | D. | Chemical Abstract 34, 7879 |
| 29 | H | H | NH | S. | |
| 30 | CH$_3$ | H | O | D. | Chemical Abstract 22, 29229 |
| 31 | H | H | N—C$_6$H$_4$—O—C$_6$H$_4$—N(maleimide) | D. | Chemical Abstract 70, 107115 P |
| 32 | H | H | N—(3-methyl-4-aminophenyl)—CH$_2$—(3-methyl-4-maleimidophenyl) | D. | Chemical Abstract 76, 141580 V |
| 33 | H | H | N—C$_6$H$_4$—N(maleimide) | D. | Chemical Abstract 54, 10385 g |
| 34 | H | H | N—C$_6$H$_4$—COOH (para) | D. | Chemical Abstract 52, 9025 a |
| 35 | H | H | N—C$_6$H$_4$—COOH (meta) | D. | Chemical Abstract 67, 44638 b |
| 36 | H | H | N—C$_6$H$_4$—OH (para) | D. | Chemical Abstract 57, 11358 g |

-continued
| Compound No. | R¹ | R² | X | F | Literature or m.p. (°C.) |
|---|---|---|---|---|---|
| 37 | H | H | 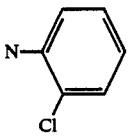 | D. | Chemical Abstract 49, 7798 f |
| 38 | H | H | 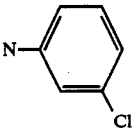 | D. | Chemical Abstract 49, 7798 f |
| 39 | H | H | 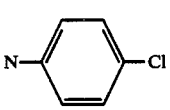 | D. | Chemical Abstract 49, 7798 f |
| 40 | H | H | 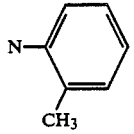 | D. | Chemical Abstract 49, 7798 f |
| 41 | H | H | 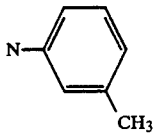 | D. | Chemical Abstract 42, 7340 d |
| 42 | H | H | 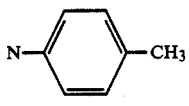 | D. | Chemical Abstract 50, 13771 g |
| 43 | H | H | 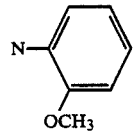 | D. | Chemical Abstract 50, 13772 a |
| 44 | H | H | 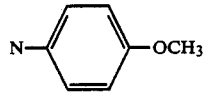 | D. | Chemical Abstract 50, 13771 g |
| 45 | H | H | 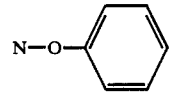 | D. | |
| 46 | H | H | 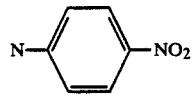 | D. | Chemical Abstract 42, 7340 e |
| 47 | H | H | 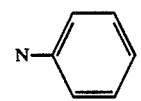 | D. | Chemical Abstract 36, 1333 |

-continued

| Compound No. | R¹ | R² | X | F | Literature or m.p. (°C.) |
|---|---|---|---|---|---|
| 48 | H | -S-C₆H₅ | -N-C₆H₅ | S. | Chemical Abstract 55, 23430 e |
| 49 | H | -S-C₆H₅ | -N-C₆H₄-Cl (3-Cl) | S. | 84–86 |
| 50 | H | -S-C₆H₅ | -N-C₆H₄-Cl (4-Cl) | S. | 153–155 |
| 51 | H | -SO₂-C₆H₅ | -N-C₆H₅ | S. | Chemical Abstract 84, 89129 c |
| 52 | H | -S-C₆H₅ | -N-C₆H₃-2,4-Cl₂ | S. | Chemical Abstract 75, 5516 f |
| 53 | H | -S-C₆H₅ | -N-C₆H₃-3,4-Cl₂ | S. | 154–155.5 |
| 54 | H | H | NH | D. | |
| 55 | H | H | NCH₂CH₃ | D. | Chemical Abstract 45, 1162 g |

The following production examples illustrate methods for production of some representative novel species of the compound of general formula (I).

PRODUCTION EXAMPLE 1

A solution of thiophenol (1.70 g) and 2-(3-chlorophenyl)maleimide (2.60 g) in ethanol (50 ml) is refluxed for 3.5 hours.

The ethanol is distilled off and the residue is recrystallized from ethanol-n-hexane to give 2-(3-chlorophenyl)-3-phenylthiosuccinimide (1.10 g), m.p. 104°–106° C.

IR (Nujol): 3150, 3050, 1780, 1695 cm⁻¹

NMR (CDCl₃, δ): 3.88, 4.05 (2H, ABq, J=6Hz), 7.00–7.67 (9H, m), 8.58 (1H, broad s).

By a procedure analogous to Production Example 1, the following compounds were obtained.

PRODUCTION EXAMPLE 2

2-(2-Chlorophenyl)-3-ethoxycarbonylmethylthio-succinimide, m.p. 115°–118° C.

IR (Nujol): 3130, 3050, 1760, 1730, 1700 cm⁻¹

NMR (CDCl₃, δ): 1.26 (3H, t, J=7Hz), 3.19, 3.75 (2H, ABq, J=15Hz), 4.16 (2H, q, J=7Hz), 4.54, 4.94 (2H, ABq, J=9Hz), 7.17–7.50 (4H, m), 8.90 (1H, broad s).

PRODUCTION EXAMPLE 3

2-(2-Chlorophenyl)-3-(2-pyridylthio)succinimide, m.p. 158°–160° C.

IR (Nujol): 3140, 3040, 1770, 1695 cm⁻¹

NMR (DMSO-d₆, δ): 4.77, 4.93 (2H, d, J=8Hz), 7.00–8.40 (8H, m), 11.83 (1H, broad s).

PRODUCTION EXAMPLE 4

2-(2-Chlorophenyl)-3-phenylthiosuccinimide, m.p. 77°–83° C.

IR (Nujol): 3130, 1780, 1695 cm⁻¹

NMR (CDCl₃, δ): 4.09, 4.28 (2H, ABq, J=7Hz), 7.00–7.67 (9H, m), 8.83 (1H, broad s).

PRODUCTION EXAMPLE 5

2-(2-Chlorophenyl)-3-(4-chlorophenylthio)-succinimide, m.p. 40°–50° C.

NMR (CDCl₃, δ): 4.12, 4.25 (2H, ABq, J=6Hz), 7.00–7.57 (8H, m), 8.80 (1H, broad s).

PRODUCTION EXAMPLE 6

2-(2-Chlorophenyl)-3-(4-methylphenylthio)-succinimide, m.p. 44°–55° C.

NMR (CDCl$_3$, δ): 2.33 (3H, s), 4.46, 4.91 (2H, ABq, J=6Hz), 6.97–7.50 (8H, m), 8.63 (1H, broad s).

PRODUCTION EXAMPLE 7

2-(2-Methylphenyl)-3-phenylthiosuccinimide, m.p. 130°–134° C.

IR (Nujol): 3170, 3060, 1790, 1700 cm$^{-1}$
NMR (CDCl$_3$, δ): 2.33 (3H, s), 3.88, 4.03 (2H, ABq, J=5Hz), 7.0–7.6 (9H, m), 8.73 (1H, broad s).

PRODUCTION EXAMPLE 8

2-Phenyl 3-phenylthiosuccinimide, m.p. 109°–112° C.
IR (Nujol): 3175, 3060, 1783, 1700 cm$^{-1}$
NMR (CDCl$_3$, δ): 3.91, 4.08 (2H, ABq, J=5Hz), 7.0–7.6 (10H, m), 8.66 (1H, broad s).

PRODUCTION EXAMPLE 9

2-(2-Methoxyphenyl)-3-phenylthiosuccinimide, m.p. 108°–110° C.
IR (Nujol): 3150, 3050, 1778, 1710 cm$^{-1}$
NMR (CDCl$_3$, δ): 3.90 (3H, s), 3.91, 4.14 (2H, ABq, J=5Hz), 6.67–7.66 (9H, m), 8.51 (1H, broad s).

PRODUCTION EXAMPLE 10

2-(4-Methoxyphenyl)-3-phenylthiosuccinimide, m.p. 108°–110° C.
IR (Nujol): 3160, 3050, 1775, 1708 cm$^{-1}$
NMR (CDCl$_3$, δ): 3.80 (3H, s), 3.91, 4.06 (2H, ABq, J=5Hz), 6.70–7.67 (9H, m), 8.60 (1H, broad s).

PRODUCTION EXAMPLE 11

2-(4-Nitrophenyl)-3-phenylthiosuccinimide, m.p. 142°–145° C.
IR (Nujol): 3190, 3050, 1785, 1695 cm$^{-1}$
NMR (CDCl$_3$, δ): 4.30 (3H, s), 4.87, 4.06 (2H, ABq, J=8Hz), 7.30–7.50 (5H, m), 7.57 (2H, d, J=8Hz), 8.17 (2H, d, J=8Hz), 11.78 (1H, broad s).

PRODUCTION EXAMPLE 12

2-(2-Nitrophenyl)-3-phenylthiosuccinimide (oil)
IR (Nujol): 3370, 1780, 1715 cm$^{-1}$
NMR (CDCl$_3$, δ): 4.11, 3.33 (2H, ABq, J=7Hz), 7.17–8.18 (9H, m), 8.57 (1H, broad s).

PRODUCTION EXAMPLE 13

A solution of mercaptothiazoline sodium (4.50 g) in tetrahydrofuran (30 ml) is added to a refluxed solution of 2-(2-chlorophenyl)maleimide (3.00 g) in tetrahydrofuran (40 ml) and the mixture is refluxed for 10 minutes. After cooling, the reaction mixture is diluted using diluted hydrochloric acid and the solvent is distilled off. The residue is extracted with ethyl acetate and the extract is washed with water and dried over magnesium sulfate. The ethyl acetate is distilled off and the residue is subjected to silica gel chromatography, elution being carried out with dichloromethanemethanol (50:1). The eluate is recrystallized from ethanol to give 2-(2-chlorophenyl)-3-(2-thiazolin-2-ylthio)succinimide (1.40 g), m.p. 195°–200° C.

IR (Nujol): 3150, 1775, 1710 cm$^{-1}$
NMR (DMSO-d$_6$, δ): 3.40 (2H, t, J=7Hz), 3.67–4.50 (2H, m), 4.93 (1H, d, J=8Hz), 6.13 (1H, d, J-8Hz), 7.17–7.67 (4H, m), 11.93 (1H, broad s).

By a procedure similar to Production Example 13, the following compounds were obtained.

PRODUCTION EXAMPLE 14

2-(2-Chlorophenyl)-3-butylthiosuccinimide, m.p. 70°–72° C.

IR (Neat): 3200, 3050, 1770, 1710 cm$^{-1}$
NMR (CDCl$_3$, δ): 0.67–1.00 (3H, m), 1.00–1.90 (4H, m), 2.80 (2H, t, J=6Hz), 3.88, 4.07 (2H, ABq, J=6Hz), 7.17–7.60 (4H, m), 8.87 (1H, m).

PRODUCTION EXAMPLE 15

2-(2-Chlorophenyl)-3-(5-methylthiazolyl-2-thio)-succinimide, m.p. 189°–193° C.

IR (Nujol): 3130, 3030, 1788, 1715 cm$^{-1}$
NMR (DNSO-d$_6$, δ): 2.50 (3H, s), 4.97 (1H, d, Hz), 6.32 (1H, d, J=7Hz), 7.17–7.66 (4H, m).

PRODUCTION EXAMPLE 16

2-(2-Chlorophenyl)-3-ethoxysuccinimide, m.p. 175° C.

IR (Nujol): 3150, 3050, 1790, 1700 cm$^{-1}$
NMR (CDCl$_3$, δ): 1.17 (3H, t, J=8Hz), 3.3–4.1 (2H, m), 4.20, 4.60 (2H, ABq, J=6Hz), 7.20–7.7 (4H, m), 8.70 (1H, broad s).

PRODUCTION EXAMPLE 17

A solution of 2-(2-chlorophenyl)maleimide (4.70 g) and aniline (3.069) in ethanol (50 ml) is refluxed for 38 hours. The reaction mixture is concentrated and the residue is subjected to silica gel chromatography, with elution being carried out with n-hexane-ethyl acetate (4:1-1:1) to give 2-(2-chlorophenyl)-3-anilinosuccinimide (oil) (3.71 g)

IR (Neat): 3500–3000, 1780, 1700 cm$^{-1}$
NMR (CDCl$_3$, δ): 4.03, 4.20 (2H, ABq, J=7Hz), 4.85 (1H, broad s), 6.3–7.6 (9H, m), 8.96 (1H, broad s).

PRODUCTION EXAMPLE 18

A solution of N-(4-chlorophenyl)maleimide (6.23 g) and thiophenol (3.31 g) in ethanol is refluxed for 1 hour. After cooling, the precipitate is collected by filtration and recrystallized from ethanol to give N-(4-chlorophenyl)-2-phenylthiosuccinimide (7.70 g), m.p. 153°–155° C.

IR (Nujol): 1690 cm$^{-1}$
NMR (CDCl$_3$, δ): 2.83 (1H, dd, J=4Hz, 19Hz), 3.35 (1H, dd, J=8Hz, 19Hz), 4.15 (1H, dd, J=4Hz, 8)Hz), 7.03 (2H, d, J=9Hz), 7.76–7.23 (7H, m).

By a procedure similar to Production Example 18, the following compounds were obtained.

PRODUCTION EXAMPLE 19

N-(3,4-Dichlorophenyl)-2-phenylthiosuccinimide, m.p. 154°–155.5° C.

IR (Nujol): 1780, 1690 cm$^{-1}$
NMR (CDCl$_3$, δ): 2.86 (1H, dd, J=4Hz, 18Hz), 3.38 (1H, dd, J=8Hz, 18Hz), 4.15 (1H, dd, J=4Hz, 8Hz), 7.80–6.80 (8H, m).

PRODUCTION EXAMPLE 20

N-(3-Chlorophenyl)-2-phenylthiosuccinimide, m.p. 84°–86° C.

IR (Nujol): 1780, 1700 cm$^{-1}$
NMR (CDCl$_3$, δ): 2.86 (1H, dd, J=4Hz, 18Hz), 3.40 (1H, dd, J=8.5Hz, 18Hz), 4.18 (1H, dd, J=4Hz, 8.5Hz), 7.90–6.80 (9H, m).

PRODUCTION EXAMPLE 21

To a solution of 2-(2-chlorophenyl)maleic anhydride (125.0 g) in acetic acid (1.2 l) is added cyclohexylamine (59.4 g) and the mixture is refluxed for 12 hours. The solvent is distilled off and the residue is dissolved in ethyl acetate (500 ml). This solution is successively washed with 5% hydrochloric acid (150 ml), sodium hydrogen carbonate solution (500 ml) and water (150 ml) and dried over magnesium sulfate. The solvent is distilled off and the residue is distilled off to give N-cyclohexyl-(2-chlorophenyl)maleimide (oil) (90.2 g), b.p. 171°–176° C./0.8 ton.

IR (Film): 1765, 1700 cm$^{-1}$

NMR (CDCl$_3$, δ): 0.8–2.6 (10H, m) 3.7–4.3 (1H, m), 6.90 (1H, s), 7.15–7.90 (4H, m).

The compound of general formula (I) has specific plant growth regulating activity (for example, an action to promote formation of the abscission layer of a matured fruit). For example, when applied to mature fruit, a composition containing this compound promotes formation of the abscission layer of the fruit without damaging the leaf and fruit, thereby causing or facilitating abscission of the mature fruit. It should also be noted that this compound does not affect immature fruit.

Therefore, the use of a plant growth regulating composition of the invention facilitates manual or mechanical harvest of fruit.

The plants to be treated for the above purpose may be fruit trees in general. For example, by applying the composition to citrus varieties (e.g. orange and kumquat), coffee, olive, pepper, nuts, etc., particularly the harvest of fruits of these plants can be facilitated.

The treatment of plants may be carried out 3 to 20 days, preferably 5 to 10 days, before harvest of fruits.

The compound of general formula (I) has weed-controlling activity and can, therefore, be used for controlling weeds such as barnyard grass, crabgrass, green foxtail, inunohuguri, chickweed, dent foxtail and so on.

Furthermore, the combined use of the compound of general formula (I) with ethephon

which has heretofore been used as an abscission agent results in a synergistic potentiation of abscission effect. Therefore, the compound of general formula (I) can be used not only as a single-agent treatment for promoting the formation of the abscission layer of fruit but also can be used in combination with ethephon for that purpose. For such combined use, about 1 to 100 parts by weight of ethephon can be appropriately used relative to 100 parts by weight of the compound of general formula (I).

While the method of use of this plant growth regulating composition is dependent on the variety of plant to be treated, it is generally appropriate to apply the composition to the entire surface of the tree. Though the proper concentration of the compound (I) also varies with the variety of plant, it is generally in the range of about 1 to 5,000 ppm and preferably about 10 to 1,000 ppm.

For field application of the plant growth regulating composition of the invention, it can be provided, as formulated with various vehicles, in forms suited to the object of use and field conditions, such as dusts, granules, tablets, wettable powders, emulsifiable concentrates and so on. The term "vehicle" is used herein to denote whichever of solid and liquid vehicles or a combination thereof. Thus, for example, talc, clay, kaolin, diatomaceous earth, calcium carbonate, potassium chlorate, niter, nitrocellulose, starch, gum arabic, water, alcohol, benzene, acetone and so on can be used as said vehicle. In addition, auxiliary agents such as spreading agents, emulsifiers, etc. can be incorporated as required.

Any preparation so obtained can be used as it is alone but may be used in admixture with fungicides, insecticides, herbicides, other plant growth regulators and/or fertilizers.

The following test examples illustrate the effects of the plant growth regulating composition of the present invention.

TEST EXAMPLE 1

(abscission effect on kumquat fruit)

A kumquat tree (height 40–50 cm) bearing about 30 fruit was planted in each pot with a diameter of 30 cm. At the maturation of the fruit, the plant growth regulating composition of the invention (an emulsifiable concentrate containing one of the under-mentioned compounds was prepared in accordance with Example 1 and diluted with water to a concentration of 500 ppm) was applied to the tree in such a manner that the entire surface of the tree would be uniformly wetted. Two trees were provided for each composition and, after spraying, the pots were placed in a green house (internal temperature 12° C.–28° C.). Five days after application, 20 fruit were plucked off from each tree by hand and the ease of plucking was scored according to the scoring schema give below. Then, based on the degrees of ease of detachment of all fruit, the average abscission value was calculated by means of the following equation. The results are set forth below in the table.

Average abscission value $$\frac{100 \times \text{(number of fruit with abscission score 1)}}{20} +$$

$$\frac{50 \times \text{(number of fruit with abscission score 2)} + 0 \times \text{(number of fruit with abscission score 3)}}{20}$$

Incidentally, application of the composition of the invention did not augment defoliation.

Fruit abscission scoring scale (degree of ease of plucking)

1: Easy to pluck off (without injury to the fruit skin and plant region adjacent to abscission layer)

2: Fairly easy to pluck off (limited injury to fruit skin and plant region adjacent to abscission layer)

3: Difficult to pluck off (major injury to fruit skin)

| Compound No. | Average abscission value |
|---|---|
| 1 | 87.5 |
| 2 | 97.5 |
| 5 | 64.0 |
| 9 | 63.0 |
| 12 | 51.5 |
| 13 | 82.5 |
| 14 | 92.5 |
| 15 | 89.5 |
| 18 | 60.6 |
| 19 | 53.5 |
| 20 | 55.0 |
| 28 | 63.0 |
| 31 | 77.5 |
| 35 | 67.5 |
| 36 | 70.0 |
| 38 | 96.0 |
| 39 | 96.5 |
| 41 | 86.0 |
| 42 | 85.5 |
| 44 | 79.0 |
| 46 | 58.0 |

-continued

| Compound No. | Average abscission value |
|---|---|
| 47 | 95.5 |
| 54 | 81.0 |
| 55 | 78.0 |
| Untreated | 0 |

TEST EXAMPLE 2

(A study of kumquat abscission and defoliation by the combined use of ethephon with the plant growth regulator of the invention)

An abscission test of kumquat fruit was performed under the same conditions as Test Example 1 except that ethephon was used in combination with the plant growth regulator of the invention. To prepare test solutions, ethephon was added to each of the diluted emulsions used in Test Example 1 at the level of 25 ppm or 100 ppm. The ethephon used was a commercial product (Nissan Chemical, 10%).

In a defoliation survey simultaneously conducted, the percentage of the number of fallen leaves at 10 days after application relative to the number of leaves on the sample tree immediately before application was calculated and is shown in parentheses in the following table.

The results are set forth below in the table. In the table, the plant growth regulating composition of the invention is designated by compound No.

| Compound No. | Concentration (ppm) | Ethephon (ppm) 0 | 25 | 100 |
|---|---|---|---|---|
| 1 | 0 | 0(0.8) | 10.5(1.3) | 48.0(6.8) |
|  | 300 | 54.0(0.9) | 91.5(1.6) | 100(8.0) |
|  | 500 | 97.5(0.9) | 100(1.5) | 100(8.2) |
| 14 | 0 | 0(0.8) | 10.5(1.3) | 48.0(6.8) |
|  | 300 | 47.0(0.8) | 94.0(1.4) | 100(7.2) |
|  | 500 | 93.0(1.0) | 100(1.4) | 100(7.7) |
| 38 | 0 | 0(0.8) | 10.5(1.3) | 48.0(6.8) |
|  | 300 | 55.0(0.7) | 96.0(1.1) | 100(7.7) |
|  | 500 | 96.0(1.0) | 100(1.6) | 100(6.9) |

TEST EXAMPLE 3

(Growth inhibition by treatment at seed germination)

A filter paper was set in the bottom of a dish with a diameter of 7 cm and the plant growth regulator of the invention (prepared by dissolving a predetermined amount of one of the compounds indicated below in the table in 0.5 ml of acetone). After evaporation of the acetone, 5 ml of water was added and, then, 10 seeds of barnyard grass were placed on the filter paper and allowed to germinate and grow at 25° C. for 7 days. During this period, the seeds were exposed to fluorescent light (4,000 lux). After 7 days, the fresh weight of each seedling is determined and its percentage based on the fresh weight of the untreated seedling was calculated. Based on the data, the degree of growth inhibition was scored according to the following scheme. The results are shown below in the table.

| Growth inhibition scale | |
|---|---|
| 3: | 0–25% of untreated control |
| 2: | 26–50% |
| 1: | 51–75% |
| 0: | ≧76% |

| Plant growth regulator of the invention Compound No. | Growth inhibition score 1 mg | 5 mg |
|---|---|---|
| 1 | 2 | 3 |
| 2 | 2 | 3 |
| 13 | 1 | 3 |
| 14 | 1 | 3 |
| 15 | 2 | 3 |
| 38 | 1 | 3 |
| 39 | 2 | 3 |
| 41 | 1 | 3 |
| 42 | 1 | 3 |
| 54 | 3 | 3 |
| 55 | 2 | 3 |

TEST EXAMPLE 4

An abscission test on *Citrus Tamurana* Takahashi was performed under the field conditions. At the maturation of the fruit, the plant growth regulating composition of the invention (an emulsifiable concentrate containing the compound of this invention was prepared in accordance with Example 1 and diluted with water to a concentrate of 500 ppm) was sprayed to the tree in such a manner that the entire surface of the tree would be uniformly wetted. Two trees (10 year old) were provided for each composition. Six days after application, 20 fruits were plucked off from each tree by hand and the ease of plucking was scored in the same method as that of Test Example 1. The results are set forth in the following table.

| compound No. | Concentration (ppm) | Average abscission value |
|---|---|---|
| 1 | 500 | 83.5 |
| 14 | 500 | 50.0 |
| untreated |  | 0 |

The following examples are further illustrative of the presence invention.

EXAMPLE 1

(emulsifiable concentrate)

| 2-(4-Chlorophenyl)-3-phenylthiosuccinimide | 20 parts |
|---|---|
| Xylene | 30 parts |
| Isophorone | 30 parts |
| Sorpol 9048 | 20 parts |

The above ingredients were mixed to give an emulsifiable concentrate.

EXAMPLE 2

(wettable powder)

| 2-(4-Chlorophenyl)-3-phenylthiosuccinimide | 20 parts |
|---|---|
| Sodium ligninsulfonate | 2 parts |
| Polyoxyethylene alkyl ether | 2 parts |
| Zeaklite | 76 parts |

The above ingredients were mixed to give a wettable powder.

We claim:

1. A method for regulating plant growth which is characterized by treating a plant with an effective, regulating amount of a composition containing the compound:

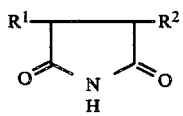

wherein $R^1$ is halophenyl and $R^2$ is phenylthio, in admixture with a vehicle.

2. A method for regulating plant growth as claimed in claim 1, wherein plant is citrus.

3. A method for regulating plant growth as claimed in claim 1, wherein citrus is orange.

4. A method for regulating plant growth as claimed in claim 1, wherein plant is citrus.

5. A method for regulating plant growth as claimed in claim 4, wherein citrus is orange.

6. A method for regulating plant growth as claimed in claim 1, wherein the regulating activity is one to form abscission layer for fruit harvest aid.

7. A method for regulating plant growth as claimed in claim 6, wherein fruit is citrus.

8. A method for regulating plant growth as claimed in claim 7, wherein citrus is orange.

9. A method for regulating plant growth as claimed in claim 1, wherein the regulating activity is one to form abscission layer for fruit harvest aid.

10. A method for regulating plant growth as claimed in claim 9, wherein fruit is citrus.

11. A method for regulating plant growth as claimed in claim 10, wherein citrus is orange.

12. The method of claim 1, wherein $R^1$ is 4-chlorophenyl.

* * * * *